United States Patent
Deur-Bert et al.

(10) Patent No.: US 9,624,145 B2
(45) Date of Patent: *Apr. 18, 2017

(54) PROCESS FOR THE MANUFACTURE OF 2,3,3,3-TETRAFLUOROPROPENE BY GAS PHASE FLUORINATION OF PENTACHLOROPROPANE

(71) Applicant: Arkema France, Colombes (FR)

(72) Inventors: Dominique Deur-Bert, Charly (FR); Anne Pigamo, Francheville (FR); Nicolas Doucet, Lyons (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,896

(22) Filed: Jan. 28, 2016

(65) Prior Publication Data

US 2016/0145175 A1    May 26, 2016

Related U.S. Application Data

(63) Continuation of application No. 13/980,669, filed as application No. PCT/IB2011/000313 on Jan. 21, 2011, now Pat. No. 9,278,895.

(51) Int. Cl.
| | |
|---|---|
| *C07C 17/25* | (2006.01) |
| *C07C 17/20* | (2006.01) |
| *C07C 17/383* | (2006.01) |
| *C07C 17/42* | (2006.01) |

(52) U.S. Cl.
CPC ......... *C07C 17/206* (2013.01); *C07C 17/25* (2013.01); *C07C 17/383* (2013.01); *C07C 17/42* (2013.01)

(58) Field of Classification Search
CPC ........ C07C 17/25; C07C 17/206; C07C 17/20
See application file for complete search history.

(56) References Cited

U.S. PATENT DOCUMENTS

| | | | |
|---|---|---|---|
| 4,902,838 A | 2/1990 | Manzer et al. | |
| 5,523,500 A | 6/1996 | Cheminal et al. | |
| 5,811,603 A | 9/1998 | Elsheikh | |
| 9,278,895 B2 * | 3/2016 | Deur-Bert ............. | C07C 17/206 |
| 2007/0197842 A1 | 8/2007 | Mukhopadhyay et al. | |
| 2009/0030244 A1 | 1/2009 | Merkel et al. | |
| 2009/0287026 A1 | 11/2009 | Kopkalli et al. | |
| 2011/0245548 A1 | 10/2011 | Merkel et al. | |
| 2013/0267740 A1 | 10/2013 | Wendlinger et al. | |

FOREIGN PATENT DOCUMENTS

| | | |
|---|---|---|
| EP | 0 939 071 | 9/1999 |
| EP | 2 103 587 | 9/2009 |
| GB | 1091103 | 11/1967 |

(Continued)

OTHER PUBLICATIONS

International Search Report dated Nov. 16, 2011 for PCT/IB2011/000313.

*Primary Examiner* — Jafar Parsa
*Assistant Examiner* — Medhanit Bahta
(74) *Attorney, Agent, or Firm* — Brinks Gilson & Lione

(57) ABSTRACT

The present invention provides a process of catalytic fluorination in gas phase of product 1,1,1,2,3-pentachloropropane or/and 1,1,2,2,3-pentachloropropane into product 2,3,3,3-tetrafluoropropene in presence of a catalyst.

12 Claims, 2 Drawing Sheets

(56) References Cited

FOREIGN PATENT DOCUMENTS

| | | |
|---|---|---|
| WO | WO 2005/108334 | 11/2005 |
| WO | WO 2007/079431 | 7/2007 |
| WO | WO 2008/040969 | 4/2008 |
| WO | WO 2008/054781 | 5/2008 |
| WO | WO 2009/003084 | 12/2008 |
| WO | WO 2009/003157 | 12/2008 |
| WO | WO 2009/015317 | 1/2009 |
| WO | WO 2009/018561 | 2/2009 |
| WO | WO 2009/118628 | 10/2009 |
| WO | WO 2010/123148 | 10/2010 |

* cited by examiner

PROCESS FOR THE MANUFACTURE OF 2,3,3,3-TETRAFLUOROPROPENE BY GAS PHASE FLUORINATION OF PENTACHLOROPROPANE

CROSS-REFERENCE TO RELATED APPLICATIONS

This application is a Continuation of U.S. patent application Ser. No. 13/980,669 filed Sep. 26, 2013, now allowed; which is a National Stage application of International Application No. PCT/IB2011/000313 filed Jan. 21, 2011.

FIELD OF THE INVENTION

The aim of the invention is the catalytic fluorination in gas phase of product 1,1,1,2,3-pentachloropropane (HCC 240db) and/or 1,1,2,2,3-pentachloropropane (HOC 240aa) into product 2,3,3,3-tetrafluoropropene (HOFO 1234yf).

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies, which present a low ODE (ozone depletion potential) and a low GWP (global warming potential.) Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODE and GWP values.

Several processes for production of HFOs compounds, in particular of propenes, were developed. The two compounds 1233xf (2-chloro-3,3,3-trifluoropropene) and 1234yf (2,3,3,3-tetrafluoropropene) are particularly desired.

US2009/0240090 discloses the gas-phase reaction of 1,1,1,2,3-pentachloropropane (HCC 240db) into product 2-chloro-3,3,3-trifluoropropene (HCFO 1233xf) (in the absence of oxygen). The catalyst used in Example 3 is fluorinated $Cr_2O_3$. The product 1233xf thus produced is then converted into product 2-chloro-1,1,1,2-tetrafluoropropane (244bb) in a liquid phase reaction.

WO200.9/015317 discloses the reaction of a chlorinated compound, which can be 1,1,2,3-tetrachloro-1-propene (1230xa), 1,1,1,2,3-pentachloropropane (240db) or 2,3,3,3-tetrachloro-1-propene (1230xf) with HF, in gas phase, on a catalyst and in the presence of at least one stablizer. This process allows obtaining 2-Chloro-3,3-trifluoro-1-propene (1233xf). No working example is provided with 240db as a starting material. The stabilizer is said to improve catalyst lifetime. It is also mentioned that periodic regeneration is considered.

WO2005/108334, example 3, discloses that 240db is passed through a flow reactor for a contact time for about 5 to 50 seconds at about 250-400° C. in the presence of 5 molar excess of HF over a 50 g ⅛-inch $Cr_2O_3$ catalyst bed to give 244db (2-chloro-1,1,1,3-tetrafluoropropane). It is further indicated that the 244db is then dehydrochlorinated by passing it over a $Cr_2O_3$ catalyst (50 g) at 425-550° C. with a contact time of 25 to 30 seconds to afford product 1234ze (1,3,3,3-tetrafluoropropene).

GB-A-1091103 discloses a process for manufacturing a chromium fluorination catalyst. Numerous compounds that may be fluorinated using this catalyst are indicated: pentachloropropane is mentioned among others, while not being the preferred compound.

WO2010/123148 discloses the fluorination of 240db into 1293xf, in the absence of catalyst.

Thus, there is still a need for processes for the production of compound 1234yf.

SUMMARY OF THE INVENTION

The invention provides single stage process of catalytic fluorination in gas phase of product. 1,1,1,2,3-pentachloropropane or/and 1,1,2,2,3-pentachloropropane into product 2,3,3,3-tetrafluoropropene in presence of a catalyst, where the process is preferably continuous. The process is a single stage process, preferably carried out in one reactor, more preferably in one catalytic bed.

Embodiments are the following:
  The product 2,3,3,3-tetrafluoropropene is present at a concentration of at least 1%, preferably more than 2%, more preferably more than 3%.
  The catalyst is a chromium catalyst, supported or unsupported, preferably unsupported.
  The catalyst further comprises a co-catalyst selected from Ni, Co, Zn, Mn, Mg or mixtures thereof, preferably nickel or magnesium, and wherein said co-catalyst is preferably present in an amount from about 1-10 wt % of said fluorination catalyst.
  The process is carried out in the presence of a catalyst comprising Ni—Cr, preferably supported
  The catalyst is supported on a support selected from fluorinated alumina, fluorinated chromia, fluorinated activated carbon or graphite carbon.
  The fluorination catalyst is activated with a fluorine-containing compound, preferably hydrogen fluoride.
  The 1,1,1,2,3-pentachloropropane contains up to 40 mol % of isomer 1,1,2,2,3-pentachloropropane.
  The process is carried out at a pressure from 3 to 20 bars, preferably 5 to 15 bars, more preferably 7 to 10 bars.
  The process is carried out at a temperature of from 200 to 450° C., preferably from 300 to 430° C., more preferably from 320 to 420° C.
  The process is carried out with a contact time from 6 to 100 sec, preferably from 10 to 80 sec, more preferably from 15 to 50 sec.
  The process is carried out with a molar ratio HF:240 from 3:1 to 150:1, preferably 4:1 to 70:1, more preferably 5:1 to 50:1.
  The process is carried out in the presence of a polymerization inhibitor, preferably chosen from the group consisting of p-methoxyphenol, t-amylphenol, limonene, d,l-limonene, quinones, hydroquinones, epoxides, amines and mixtures thereof.
  The process is carried out in the presence of oxygen and/or chlorine, preferably in an amount of from 0.05 to 15 mole %, more preferably 0.3 to 10 mole % of oxygen or chlorine per pentachloropropane molecule.
  The process comprises the steps of
    (i) contacting 1,1,1,2,3-pentachloropropane (HCC 240db) and/or 1,1,2,2,3-pentachloropropane (HCC 240aa) with hydrogen fluoride HF in gas phase in the presence of a fluorination catalyst under conditions sufficient to produce a reaction mixture comprising 2,3,3,3-tetrafluoropropene (1234yf);

(ii) separating the reaction mixture into a first stream comprising 2,3,3,3-tetrafluoropropene (1234yf) and a second stream comprising 2-chloro-3,3,3-trifluoro-1-propene (1233xf) and 1,1,1,2,2-pentafluoropropane (245cb);

(iii) recycling at least a part of the second stream at least in part back to step (i).

The process comprises the steps of:

(i) contacting 1,1,1,2,3-pentachloropropane (HCC 240db) and/or 1,1,2,2,3-pentachloropropane (HCC 240aa) with hydrogen fluoride HF in gas phase in the presence of a fluorination catalyst under conditions sufficient to produce a reaction mixture comprising 2,3,3,3-tetrafluoropropene (1234yf);

(ii) separating the reaction mixture into a first stream comprising HCl, 2,3,3,3-tetrafluoropropene (1234yf) and a second stream comprising HF, 2-chloro-3,3,3-trifluoro-1-propene (1233xf) and 1,1,1,2,2-pentafluoropropane (245cb);

(iii) recycling at least a part of the second stream at least in part back to step (i).

The first stream may be further separated into HCl and 2,3,3,3-tetrafluoropropene (1234yf), preferably in a distillation step.

The process comprises the steps of (i) contacting 1,1,1,2,3-pentachloropropane (HCC 240db) and/or 1,1,2,2,3-pentachloropropane (HCC 240aa) with hydrogen fluoride HF in gas phase in the presence of a fluorination catalyst under conditions sufficient to produce a reaction mixture comprising 2,3,3,3-tetrafluoropropene (1234yf);

(ii) separating the reaction mixture into HCl and a stream containing the fluorinated products;

(iii) separating said stream containing the fluorinated products into a first stream comprising 2,3,3,3-tetrafluoropropene (1234yf) and a second stream comprising HF, 2-chloro-3,3,3-trifluoro-1-propene (1233xf) and 1,1,1,2,2-pentafluoropropane (245cb);

(iv) recycling at least a part of the second stream at least in part back to step (i).

The separating step is a distillation step.

The process is continuous.

BRIEF DISCLOSURE OF THE DRAWINGS

DETAILED DESCRIPTION OF EMBODIMENTS

Figure 1:
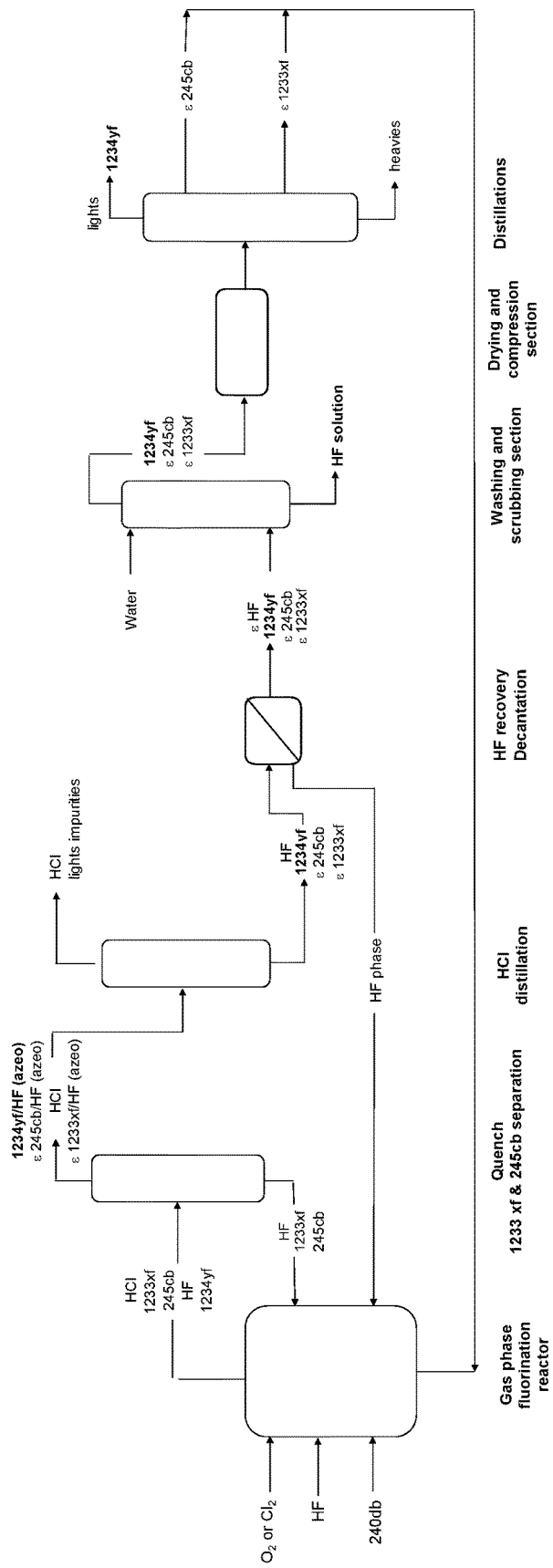
FIG. 1 is a scheme representing the process carried out in the invention.

The invention is based on the findings that 240db (and/or 240aa) can be catalytically fluorinated in gas phase in a single stage into 1234yf, and that process conditions can be selected so as to achieve a reaction down to the final product. The stream obtained typically contains at least 1% of 1234yf, preferably at least 2%, more preferably at least 3% (mol).

240db is reacted with HF in a Single reactor. The desired product is 1234yf, while 1233xf is also seen upon conversion. The 1233xf thus formed in turns undergoes a series of possible reactions. Reaction with HE can lead directly to 1234yf. This unsaturated compound upon fluorination with HF, give 245cb. 1234yf and 245cb form an equilibrium; the invention is based on this finding. Any 245cb formed can be recycled to the first reaction zone, whereby the equilibrium is displaced (1234yf being thus prevented from further conversion into 245cb). The 245cb flow rate in the recycling loop (either at the exit of the gas-phase reactor or in the second stream back exiting the distallation column and back to the gas-phase reactor) is thus substantially constant. No 245cb build up will thus take place in the recycling loop. In this instance, 240db fed into the reactor converts only into 1234yf (and possibly into 1233xf) since 245cb is already present in the recycling loop.

The catalyst used in the invention is for example a catalyst based on a metal including a transition metal oxide or a derivative or halide or oxyhalide such a metal. Catalysts are e.g. $FeCl_3$, chromium oxyfluoride, chromium oxides (that can optionally be subject to fluorination treatments), chromium fluorides, and mixtures thereof. Other possible catalysts are the catalysts supported on carbon catalysts based on antimony, catalysts based on aluminum (as $AlF_3$ and $Al_2O_3$ and oxyfluoride of alumina and aluminum, fluoride). Generally speaking, catalysts that can be used are chromium oxyfluoride, aluminium fluoride and oxyfluoride, and supported or unsupported catalyst containing a metal such as Cr, Ni, Zn, Ti, V, Zr, Mo, Ge, Sn, Pb, Mg. Reference can also be made to the disclosures of WO-A-2007/079431, at page 7, lines 1-5 and 28-32, EP-A-939071, at paragraph [0022], WO2008/054781 at page 9 line 22 to page 10 line 34, WO2008/040969 in claim 1, all incorporated herein by reference.

Prior to its use, the catalyst is subjected to activation, typically with HF, under suitable conditions.

A preferred embodiment uses a particular catalyst, which is a mixed catalyst, containing both chromium and nickel. The molar ratio Cr:Ni, with respect to the metallic element is generally between 0.5 and 5, for example between 0.7 and 2, including close to 1 The catalyst may contain in weight from 0.5 to 20% chromium and 0.5 to 20% nickel, preferably between 2 and 10% of each metal.

The metal may be present in metallic form or as derivatives, including oxide, halide or oxyhalide. These derivatives, including halide and halide oxides, are obtained by activation of the catalytic metal. Although the activation of the metal is not necessary, it is preferred.

The support is preferably made from aluminum. There are several possible carriers such as alumina, activated alumina or aluminum derivatives. These derivatives include aluminum halides and halide oxides of aluminum, for example described in U.S. Pat. No. 4,902,838, or obtained by the activation process described below.

The catalyst may include chromium and nickel in a non-activated or activated form, on a support that has been subjected to activation or not.

Reference can be made to WO2009/118628, and especially to the disclosure of the catalyst from page 4, line 30 to page 7, line 16, which is incorporated herein by reference.

The catalyst can also be a high surface area Cr based catalyst which is preferably unsupported. The catalyst can optionally contain a low level of one or more co-catalyst such as Co, Zn, Mn, Mg and Ni salt. A preferred co-catalyst is nickel or magnesium. Another preferred co-catalyst is Zn. Another preferred co-catalyst is Mg. A disclosure of the high surface area Cr based catalyst can be found in WO2009/158321, pages 4 and 6).

The process of the present invention is preferably run continuously, which from an industrial point of view is highly desirable.

The present fluorination process involves contacting 240db with HF in the reaction zone in a gas phase, under conditions sufficient to convert the 240db to fluorination products comprising mainly 1234yf.

Typically, the process of the invention is carried out with a molar ratio HF:240 from 3:1 to 150:1, preferably 4:1 to 70:1, more preferably 5:1 to 50:1.

Typically, the process of the invention is carried out at a pressure from 3 to 20 bars, preferably 5 to 15 bars, more preferably 7 to 10 bars.

Typically, the process of the invention is carried out at a temperature of from 200 to 450° C., preferably from 300 to 430° C., more preferably from 320 to 420° C. The temperature of the bed can be substantially uniform in the reactor or can be adjusted along the path of the stream, decreasing or increasing along the direction of flow.

Contact times (catalyst volume divided by the total flow rate of reactants and co-feeds, adjusted to the operating pressure and temperature) are typically from 6 to 100 sec, preferably from 10 to 80 sec, more preferably from 15 to 50 sec.

Conditions will be selected so as to promote the formation of the fully fluorinated product. When low HF:organics ratios are used, longer contact times and higher pressure will generally be used, and especially higher temperatures. High temperatures, typically above 360° C. with high pressure typically above 5 bars are generally preferred. Mild fluorination conditions may provide the 1233xf product, as is disclosed in the applicant's own patent application PCT/FR2010/052277

An oxygen or chlorine co-feed may be used to extend the catalyst lifetime, typically in an amount of from 0.05 to 15 mole %, preferably 0.5 to 10 mole % of oxygen or chlorine per pentachloropropane molecule. The oxygen can be introduced as an oxygen-containing gas such as air, pure oxygen, or an oxygen/nitrogen mixture.

A polymerization inhibitor can be used to extend the catalyst life, typically in a concentration of from about 50-1000 ppm, more preferably between 100-500 ppm. The polymerization inhibitor can be p-methoxyphenol, t-amylphenol, limonene, d,l-limonene, quinones, hydroquinones, epoxides, amines and mixtures thereof. The preferred polymerization inhibitor is p-methoxyphenol or t-amylphenol. The co-feeding of a low level of a polymerization inhibitor can control such polymerization of chloroolefins and extend the life of the catalyst as described in U.S. Pat. No. 5,714,651, incorporated herein by reference.

1233xf may be produced along with 1234yf, and separation and recycling of 1233xf and 245cb into the gas phase reactor is one embodiment of the invention.

Hence, the invention also provides for a process comprising the steps of
(i) contacting 1,1,1,2,3 pentachloropropane (HCC 240db) and/or 1,1,2,2,3-pentachloropropane (HCC 240aa) with hydrogen fluoride HF in gas phase in the presence of a fluorination catalyst under conditions sufficient to produce a reaction mixture comprising 2,3,3,3-tetrafluoropropene (1234yf).
(ii) separating the reaction mixture into a first stream comprising 2,3,3,3-tetrafluoropropene (1234yf) and a second stream comprising 2-chloro-3,3,3-trifluoro-1-propene (1233xf);
(iii) recycling at least a part of the second stream at least in part back to step (i).

This recycling can take various forms, as is depicted in the following figures.

FIG. 1 represents an embodiment of the process carried out in the invention. The gas-phase reactor is fed with 240db and HF. The reaction mixture exiting the reactor mainly comprises HCl, 1233xf, unreacted HF, 1234yf and 245cb. This reaction stream is separated by distillation into a first stream. (light, products) comprising HCl, 1234yf (possibly with a small amount of HF thereby forming an azeotropic mixture) and minor amounts of 245cb and 1233xf. A second, heavier, stream is obtained at the bottom of the distillation column, and comprises mainly HF, 1233xf and 245cb. The lighter fraction containing HCl, 1234yf (with HF) and minor amounts other products is again distillated. The top flow comprises HCl, while the bottom flow comprises 1234yf and HF, which can again be separated using appropriate known methods. Among known methods is the decantation, which produces an HF rich flow which can be recycled, to the gas-phase reactor. This decreases the fluorine content downstream in the process, generating less side-product (e.g. $CaF_2$ which must be discarded). The streams exiting the decantation are treated according to known methods, including washing and scrubbing and distillations.

Figure 2:
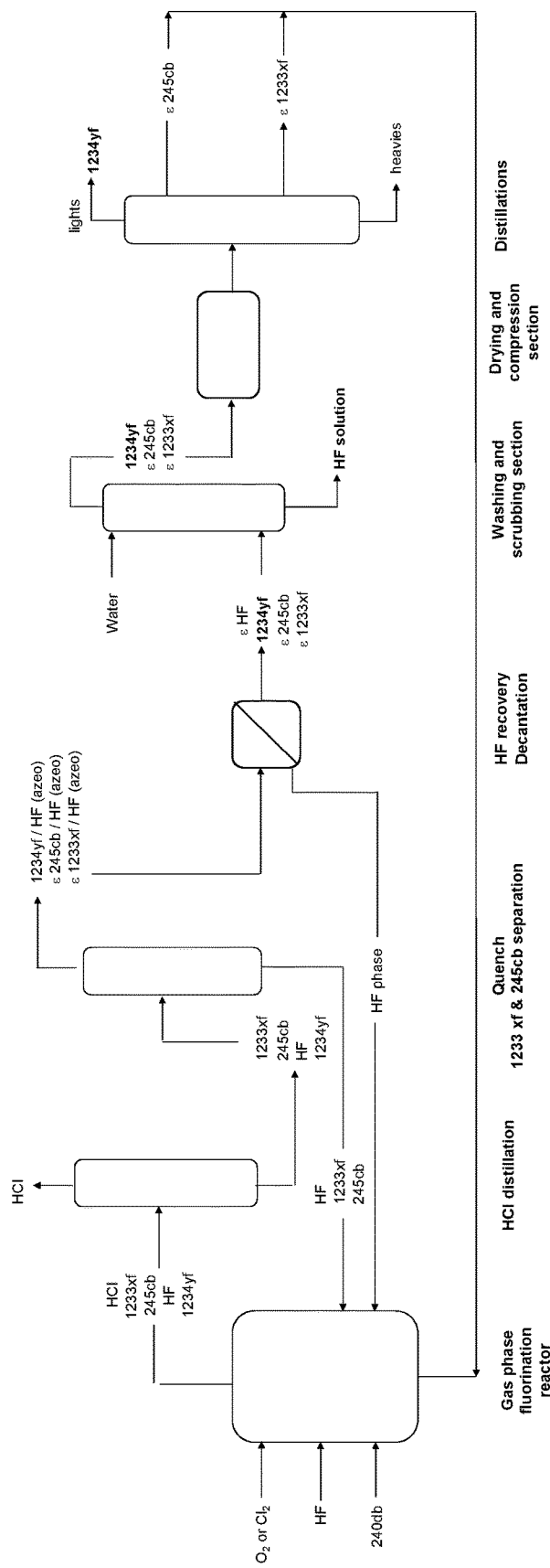
FIG. 2 is a scheme representing the process carried out in the invention.

FIG. 2 represents another embodiment, where HCl is removed in a first step before distillation of the organic fluorinated products takes place. The gas-phase reactor is fed with 240db and HF. The reaction mixture exiting the reactor comprises mainly HCl, 1233xf, unreacted HF, 1234yf and 245cb. This reaction stream is separated by a first distillation into a stream containing mainly HCl and another stream containing the other products. This other stream is separated by distillation into a first stream (light products) comprising 1234yf (possibly with a small amount of HF thereby forming an azeotropic mixture) and minor amounts of 245cb and 1233xf. A second, heavier, stream is obtained at the bottom of the distillation column, and comprises mainly HF, 1233xf and 245cb. The lighter fraction containing 1234yf (with HF) and minor amounts other products is obtained at the top of the second distillation tower. This top flow can again be separated using appropriate known methods. Among known methods is the decantation, which produces a flow of HF which can be recycled to the gas-phase reactor. This decreases the fluorine content downstream in the process, generating less side-product (e.g. $CaF_2$ which must be discarded.). The streams exiting the decantation are treated according to known methods, including washing and scrubbing and distillations.

The reactants can be fed to the reactor at the same location, at different locations, or using staged feeding at staged locations along the reactor. A preferred feeding system is to blow the gaseous reactants at the bottom of the reactor. Recycling can be done at the entry of the reactor or at an intermediate stage of the reactor; preferably at the entry of the reactor. It is also possible to recycle part of the stream exiting the reactor.

Reactions are implemented in a dedicated reactor for reactions involving halogens. Such reactors are known to those skilled in the art and can include, linings based e.g. Hastelloy®, Inconel®, Monel® or fluoropolymers. The reactor may also include means of heat exchange, if necessary.

The final product is readily recovered by any means known in the art, such as by scrubbing, washing, extraction, decantation and preferably distillation. It can also be further purified by distillation techniques.

EXAMPLES

The following examples illustrate the invention without limiting it.

The equipment used consists of a tubular reactor of an internal diameter of 28 mm, made of INCONEL® alloy 600 surrounded by a tubular oven. The homogeneity of temperature is ensured by fluidized corindon filling the space between the reactor and the oven. It is also equipped with pressure and temperature controller. The reactants, preliminarily vaporized thanks a heater, are introduced in gaseous phase at the bottom of the reactor. After the reactor, a regulation, pressure valve allows working in a range of pressure between atmospheric and 16 bars absolute.

At the outlet of the set-up, the products of the reaction are washed through a water scrubber to remove hydracids. A sample is taken to be analyzed off-line by a gas phase chromatography. Two different GC analysis are necessary to detect the wide range of possible products: the boiling point can vary from −28.3° C. for the 1234yf to 192° C. for the raw material, 240db.

The analysis by chromatography is carried out using a column CP Sil 8CB, dimensions 50 m*0.32 mm*5 µm, for the detection of heavier products like 240db. The programming of temperature of the oven is the following one: 70° C. during 10 min then slope of 10° C./min until 2.50° C.

The analysis by chromatography is carried out using a column Carbopack B 1% SP1000-60/80 mesh-5 m for quantification and better separation of lighter products. The programming of temperature of the oven is the following one: 40° C. during 10 min. then slope of 4 C./min until 180° C.

The resulting composition is given in molar %.

The molar ratio of HF (MR HF) is defined as the ratio between the molar flow rate of HF and the molar flow rate of 1,1,1,2,3-pentachloropropane.

Example 1

Not According to the Invention

Fluorination of 240db (1,1,1,2,3-pentachloropropane) is performed in the reactor described above with 79.4 cm of Ni—Cr catalyst supported on $AlF_3$.

The catalyst used is a mixed catalyst nickel/chromium of atomic ratio of Ni/Cr=1, supported on alumina fluoride and is prepared by impregnating solutions of nickel and chromic anhydride ($CrO_3$). After impregnation and drying, the Solid is treated at a temperature between 320° C. and 390° C. in the presence of a mixture of hydrofluoric acid and nitrogen (concentration by volume of 5 to 10% of this acid in nitrogen.).

The reactor was continuously fed with 15 g/hr of anhydrous HF and about 4.5 g/hr of 1,1,1,2,3-pentachloropropane at atmospheric pressure for 86 hrs. Thus, the contact time is 7.4 seconds, the molar ratio of HF to 240 is 36, and the reaction temperature is 340° C. The amount of oxygen is about 4 mol % with respect to the 240db. Results are given in the table 1.

Example 2

Not According to the Invention

Fluorination of the mixture of 65.9 mol % of 240db or 1,1,1,2,3-pentachloropropane and 34.9 mol % of 240aa or 1,1,2,2,3-pentachloropropane is performed according to example 1 described above. The reactor was continuously fed with 16 g/hr of anhydrous HF and about 5.1 g/hr of 1,1,1,2,3-pentachloropropane at atmospheric pressure. Thus, the contact time is 6.9 seconds, the molar ratio is 34, and the reaction temperature is from 340° C. The amount of oxygen is about 4 mol % with respect to the total number of mole, of 1,1,1,2,3-pentachloropropane and 1,1,2,2,3-penfachloropropane. Results are given in table 1.

Examples 3 and 4

Not According to the Invention

Example 2 is repeated at different temperatures as indicated in table 1.

TABLE 1

| | | Outlet gas molar composition (%) | | | |
|---|---|---|---|---|---|
| | Temp. ° C. | pentachloropropane | 1234yf + 245cb | 1233xf | Others |
| Ex .1 | 340 | 0 | 1.6 | 98.3 | 0 |
| Ex. 2 | 340 | 0 | 0.5 | 72.0 | 25.6 |
| Ex. 3 | 360 | 0 | 0.5 | 72.0 | 25.1 |
| Ex. 4 | 380 | 0 | 0.6 | 74.3 | 22.8 |

Use of a low pressure together with rather low temperature does not allow 1234yf to be produced in significant amount.

Example 5

According to the Invention

Fluorination of 240db (1,1,1,2,3-pentachloropropane) is performed in the reactor described above with 150 cm of Ni—Cr catalyst supported on $AlF_3$.

The catalyst used is a mixed catalyst nickel/chromium of atomic ratio of Ni/Cr=1, supported on alumina fluoride and is prepared by impregnating solutions of nickel and chromic anhydride ($CrO_3$). After impregnation and drying, the solid is treated at a temperature between 320° C. and 390° C. in the presence of a mixture of hydrofluorc acid and nitrogen (concentration by volume of 5 to 10% of this acid in nitrogen).

The reactor was continuously fed with 33 g/hr of anhydrous HF and about 3.9 g/hr of 1,1,1,2,3-pentachlotopropane at 3 bars absolute for 550 hrs. Thus, the contact time is 20 seconds, the molar ratio of HF to 240 is 40, and the reaction temperature is 300° C. The amount of oxygen is about 4 mol % with respect to the 240db. Results are given in the table. 2.

TABLE 2

| outlet gas composition with time. | | | | | | |
|---|---|---|---|---|---|---|
| Catalyst age | Outlet gas molar composition (%) | | | | | |
| (h) | $CO_2$ | 245cb | 1234yf | 1233xf | 243db | X* |
| 23 | 0.41 | 2.2 | 2.2 | 92.6 | 0.05 | 2.54 |
| 49 | 0.39 | 1.4 | 1.9 | 93.7 | 0.54 | 2.07 |
| 71 | 0.37 | 0.92 | 1.7 | 94.2 | 0.67 | 2.14 |
| 96 | 0.29 | 0.69 | 1.4 | 94.8 | 0.74 | 2.08 |

Products X include 143a, 1234ze, 245fa, 152a, 1233zd, 243ab, 1232xf, 1223xd. 240db was never detected.

Example 6

Example 5 is repeated at different temperatures as indicated in table 3. Points are recorded after around 200 h run.

| T | Outlet gas molar composition (%) | | | | |
|---|---|---|---|---|---|
| (° C.) | 245cb | 1234yf | 1233xf | 243db | X |
| 326 | 0.40 | 1.46 | 95.3 | 0.33 | 1.69 |
| 350 | 0.88 | 2.29 | 94.3 | 0.14 | 1.15 |
| 374 | 0.79 | 2.81 | 93.4 | 0.13 | 1.68 |

Products X include 143a, 1234ze, 245fa, 152a, 1233zd, 243ab, 1232xf, 1223xd. 240db was never detected.

Table 3. Impact of temperature of the reaction on the gas composition.

The increase of the temperature helps the fluorination towards 1234yf and 245cb.

Example 7

This example provides the effect, of recycling.

Fluorination is performed in the reactor described above with 100 cm of Ni—Cr catalyst supported on $AlF_3$. The pressure is 8 bars absolute and the temperature is 350° C. The contact time is 20 s, the molar ratio of HF to the sum of the organics is around 40 and the molar ratio of oxygen to the sum of the organics is 4%. The molar composition between the inlet and the outlet is given in table 4. The products that are recycled contain 1233xf and 245cb. Table 4 contains the expected data obtained by recycling.

TABLE 4

| Mol % | 240db | 1233xf | 1234yf | 245cb | 243db | others |
|---|---|---|---|---|---|---|
| Inlet | 50 | 47.5 | 0.3 | 0.1 | 0.7 | 1.4 |
| Outlet | 0 | 86.0 | 3.8 | 5.2 | 1.3 | 3.7 |

The invention claimed is:

1. A process for producing 2,3,3,3-tetrafluoropropene (1234yf) comprising:
    introducing 1,1,1,2,3-pentachloropropane (240db) and/or 1,1,2,2,3-pentachloropropane (240aa), HF, 1,1,1,2,2-pentafluoropropane (245cb) and 2-chloro-3,3,3-trifluoropropene (1233xf) into a gas phase fluorination reactor containing a fluorination catalyst, wherein the 245cb introduced to the reactor is provided from a recycle loop, and
    producing 1234yf and 1233xf in the reactor, wherein 1234yf and the recycled 245cb form an equilibrium in the reactor thus resulting in increased production of 1234yf and a constant rate of 245cb in the recycle loop.

2. The process of claim 1, wherein the process is carried out in a single stage.

3. The process of claim 1, wherein the product 2,3,3,3-tetrafluoropropene is present at a concentration of at least 1%.

4. The process of claim 1, wherein said catalyst is a chromium catalyst.

5. The process of claim 4, wherein said catalyst further comprises a co-catalyst selected from the group consisting of Ni, Co, Zn, Mn, Mg and mixtures thereof, and wherein said co-catalyst is present in an amount from about 1-10 wt % of said fluorination catalyst.

6. The process of claim 1, wherein the process is carried out in the presence of a catalyst comprising Ni—Cr.

7. The process of claim 1, wherein said catalyst is supported on a support comprising fluorinated alumina, fluorinated chromia, fluorinated activated carbon or graphite carbon.

8. The process of claim 1, wherein the fluorination catalyst is activated with a fluorine-containing compound.

9. The process of claim 1, wherein the 1,1,1,2,3-pentachloropropane contains up to 40 mol % of isomer 1,1,2,2,3-pentachloropropane.

10. The process of claim 1, wherein the process is carried out at a pressure from 3 to 20 bars.

11. The process of claim 1, wherein the process is carried out at a temperature of from 200 to 450° C.

12. The process of claim 11, wherein the process is carried out at a temperature of 350 to 450° C.

* * * * *